(12) United States Patent
Byatt et al.

(10) Patent No.: US 6,644,128 B1
(45) Date of Patent: Nov. 11, 2003

(54) FLOW METER

(75) Inventors: Anthony Byatt, Klingnau (CH); Thomas Kleiner, Fislisbach (CH); Daniel Matter, Brugg (CH); Philippe Prêtre, Baden-Dättwil (CH)

(73) Assignee: ABB Research Ltd, Zurich (CH)

( * ) Notice: Subject to any disclaimer, the term of this patent is extended or adjusted under 35 U.S.C. 154(b) by 0 days.

(21) Appl. No.: 09/808,136

(22) Filed: Mar. 15, 2001

(30) Foreign Application Priority Data

Mar. 15, 2000 (DE) .......................................... 100 12 395

(51) Int. Cl.$^7$ ................................................ G01F 1/66
(52) U.S. Cl. ................................................... 73/861.26
(58) Field of Search ................ 73/861, 861.25–861.31, 73/602, 627, 628, 643, 32 A, 597

(56) References Cited

U.S. PATENT DOCUMENTS 4,080,837 A   3/1978  Matthias et al.
4,142,412 A * 3/1979  McLeod et al.

FOREIGN PATENT DOCUMENTS

| DE | 31 39 917  | 6/1982 |
| DE | 195 48 882 | 7/1997 |
| DE | 195 49 527 | 4/1998 |
| DE | 198 29 940 | 1/2000 |
| EP | 0 908 717  | 4/1999 |
| JP | 5-99941    | 4/1993 |

\* cited by examiner

Primary Examiner—Edward Lefkowitz
Assistant Examiner—C Dickens
(74) Attorney, Agent, or Firm—Burns, Doane, Swecker & Mathis, L.L.P.

(57) ABSTRACT

A photoacoustic effect is used in order to measure a flow rate of a flowing medium (M), in particular of natural gas. A light emitter (1) is used to produce in the medium (M) a sound wave (S) which is transmitted by the medium (M) and detected by a sound detector (2). The light emitter (1) is less exposed to the medium (M) than a diaphragm such as used in the ultrasonic method.

9 Claims, 2 Drawing Sheets

FLOW METER

This application claims priority under 35 U.S.C. §§119 and/or 365 to Appln. No. 100 12 395.3 filed in Germany on Mar. 15, 2000; the entire content of which is hereby incorporated by reference.

The invention relates to a method for measuring a flow rate of a flowing medium, and to a flow meter.

It is known to use ultrasound to determine flow rates of a flowing medium, in particular of gas. The medium is irradiated with a sound wave via a microphone, the sound wave transmitted by the medium being detected by means of a second microphone, which is arranged downstream or upstream. Piezoelectric or capacitive vibration emitters or pick-ups are preferably used as microphones. There are two measurement methods in principle. In a first method, the time interval between emission and detection of the sound wave is determined, and the flow velocity is calculated therefrom. In a second method, the Doppler effect which is caused by the flowing medium is utilized and its frequency shift is determined. Such an ultrasonic measurement is disclosed, for example in U.S. Pat. No. 4,080,837.

Measurement by means of ultrasound has the disadvantage that the microphones emitting sound must be in direct contact with the medium. Consequently, tube walls must be provided with appropriate openings in which the microphones are arranged. Since the media to be measured are also often aggressive, the microphone must be appropriately provided with a resistant protective layer. Furthermore, the microphone or its protective layer is exposed to deposits which impair the sound emission.

In the prior art, furthermore, a photoacoustic method is known for detecting pollutants in a medium. Use is made in this photoacoustic method of the fact that the pollutants and the medium absorb optically at different wavelengths. The polluted medium is therefore irradiated with focused light of a defined wavelength which is absorbed by the pollutant, but not by the medium. If pollutants are present in an irradiated volume, the absorption leads to local heating, whereupon the volume expands and emits a pressure and sound wave. This sound wave can be detected by means of microphones. Such photoacoustic methods are disclosed, for example, in DE-A-31,39,917 and EP-A-0,908,717.

It is the object of the invention to create a method for measuring a flow rate, and a flow meter of the type mentioned at the beginning, which eliminate the disadvantages of ultrasonic measurement.

In the method according to the invention, a photoacoustic effect is utilized to produce a sound wave in the medium. In this process, the medium is irradiated with light, a wavelength being used which is absorbed by the medium. The medium therefore produces the sound wave itself.

The light can be guided through a small tubular opening from a light source into the medium, so that only a minimum area need be kept clean. In addition, the flow meter can be fashioned smaller than the known flow meters based on ultrasound.

In a first variant of the method, the propagation time of a photoacoustic sound wave is measured in order to determine a flow velocity. In a preferred subvariant, a propagation time of the sound wave in the flow direction is compared with a propagation time counter to the flow direction in order to obtain a measurement independent of an instant of the generation of the sound wave.

In a second variant, a Doppler frequency change in the photoacoustic sound wave is detected in order to determine a flow velocity. In a preferred subvariant, the Doppler frequency change in the flow direction is compared with a Doppler frequency change counter to the flow direction, in order to obtain a measurement independent of an instant of the generation of the sound wave.

In a third variant of the method, the propagation time of the photoacoustic sound wave is measured independently of the flow velocity, in order to determine the density of the medium.

In a fourth variant of the method, a flow profile is set up by irradiating the medium with light beams which have focal points separated spatially from one another, an array being formed by means of the focal points.

The method according to the invention is explained in more detail below with the aid of preferred exemplary embodiments which are illustrated in the attached drawings, in which.

Figure 1:
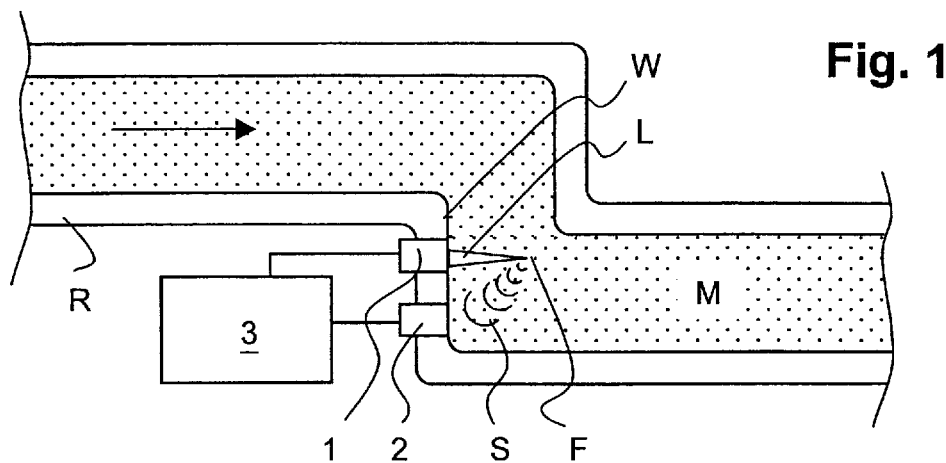
FIG. 1 is a schematic of a flow meter according to the invention and in accordance with a first embodiment.

FIG. 1 illustrates a first embodiment of the flow meter according to the invention as fitted on a tube R flowed through by a medium M. It consists essentially of at least one light emitter 1, at least one sound detector 2 and an electronic control and evaluation system 3 connected to the light emitter 1 and the sound detector 2.

The light emitter 1 is preferably a laser diode with a wavelength matched to the medium to be measured. If the medium such as, for example, natural gas, has C—H—compounds, it is preferred to select a wavelength which excites these compounds, that is to say a wavelength in the range of between 1.5 and 3.5 $\mu$m. The selection of the wavelength also depends on the density of the medium. Since the intensity of a sound wave produced by means of a photoacoustic effect is proportional to the absorption coefficient of the medium, it is possible to select a wavelength near the absorption maximum in the case of a low density, and a wavelength which is situated further from the absorption maximum in the case of a high density. The laser is preferably operated in a pulsed fashion, for example with short pulses with a duration of at least approximately 200 ns. A change in temperature of the medium which is to be expected is then typically between 0.1 and 0.2° C.

Figure 2:
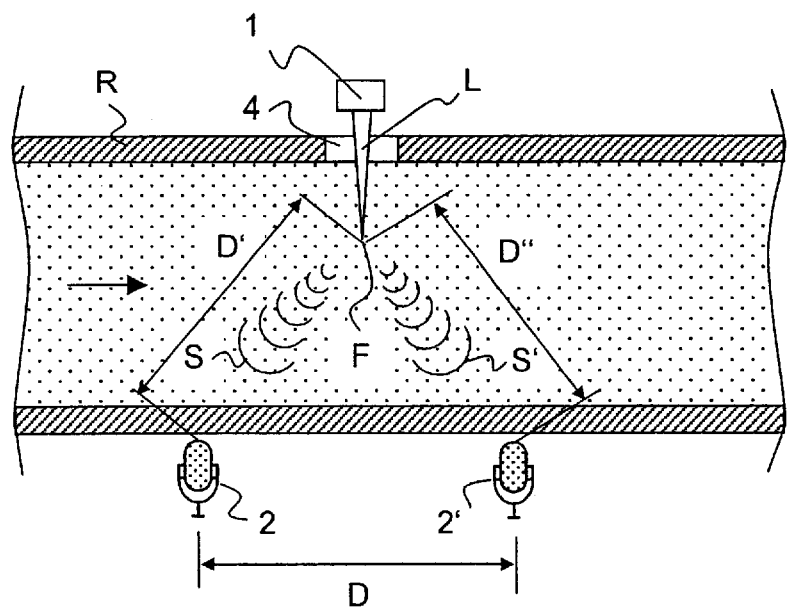
FIG. 2 is a schematic of a flow meter having two sound detectors in accordance with a second embodiment.

In this embodiment, the light emitter 1 is sunk in a wall of the tube R. In another embodiment, however, it is arranged outside the tube R and transirradiates the tube R through a suitable window 4, as is illustrated in FIG. 2. It is likewise possible to use a light source which is arranged at some distance from the tube, the light being guided to a suitable point on the tube R by means of a fiber-optic waveguide. This is advantageous when the power of the light source is sufficient to divide the light beam and to send the partial beams to a plurality of light emitters 1.

A piezoelectric or capacitive microphone can preferably be used as sound detector 2. In this case, the sound detector 2 can be sunk into the tube wall, as is illustrated in FIG. 1, or it is arranged outside the tube R, as may be seen in FIG. 2.

Only a single light emitter 1 and a single sound detector 2 are present in the embodiment in accordance with FIG. 1. Both elements are arranged in a bend of the tube R, being located on the same wall W. This wall W extends at least approximately perpendicular to a main flow direction of the medium, which is marked in the figure by an arrow.

The light emitter 1 is provided with a focusing optical system such that an emitted light beam L is focused at a focal point or focus F inside the tube. A sound wave S is produced in the medium M at this focal point F. The sound wave S produced is propagated in the medium M and reaches the sound detector 2. A time difference between an emitted light pulse and detection of the sound wave is measured. This time difference is a measure of the flow velocity given a known position of the focal point F. In another variant of the method, a Doppler frequency change is measured with the aid of the device in accordance with FIG. 1, in order to determine the flow velocity.

A light emitter 1 and two sound detectors 2, 2' are present in FIG. 2. The first sound detector 2 is used to measure the propagation time or the Doppler frequency change in the sound wave S in the flow direction of the medium M, and the second sound detector 2' is used to measure the propagation time or the Doppler frequency change counter to the flow direction. The difference between the two propagation times or the two Doppler frequency changes leads to the flow velocity in the case of a known spacing D between the two sound detectors 2, 2' and known spacings D', D" from the focal point F to the sound detectors 2, 2'. In this case, the measurement is independent of the instant of the production of sound.

Figure 3:
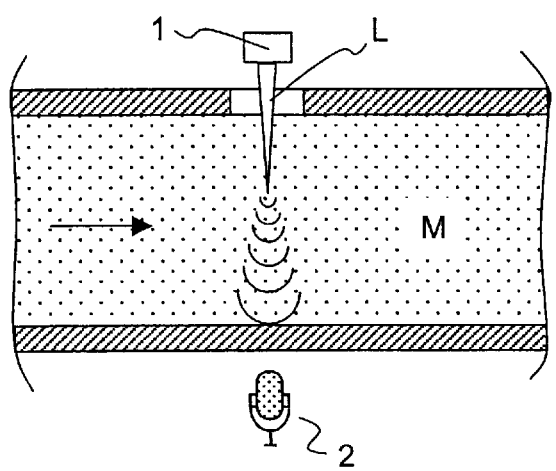
FIG. 3 is a schematic of a flow meter for determining a density of a medium in a third embodiment.

A density of the medium M can be determined in the arrangement in accordance with FIG. 3. The sound detector 2 is arranged with reference to the light emitter 1 such that the propagation time can be measured independently of the flow velocity of the medium M and thus depends essentially only on the density of the medium. In this example, the sound detector 2 and light emitter 1 are therefore arranged in a plane perpendicular to the flow direction. If the flow velocity is known, a mass flow can also be determined from the density measurement.

Figure 4:
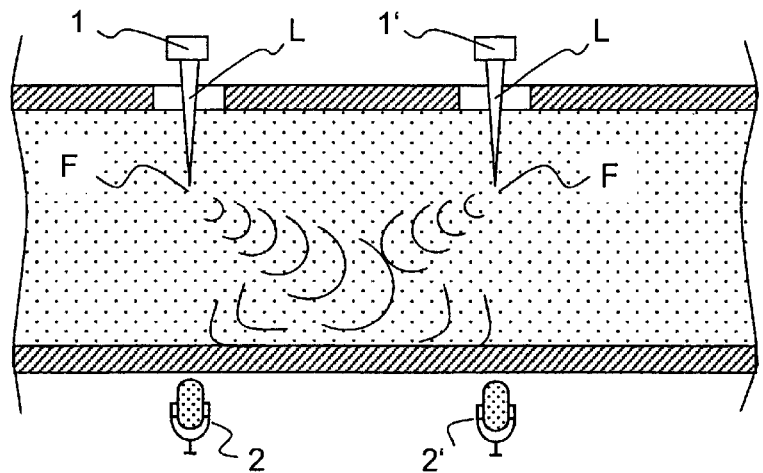
FIG. 4 is a schematic of a flow meter in a fourth embodiment.

Propagation time difference and density can be determined simultaneously in the embodiment in accordance with FIG. 4. Two light emitters 1, 1' are present for this purpose. These preferably have different powers or different wavelengths in order to produce two sound waves of different intensity such that the sound detectors can assign the signals to the individual light emitters 1, 1'.

Figure 5:
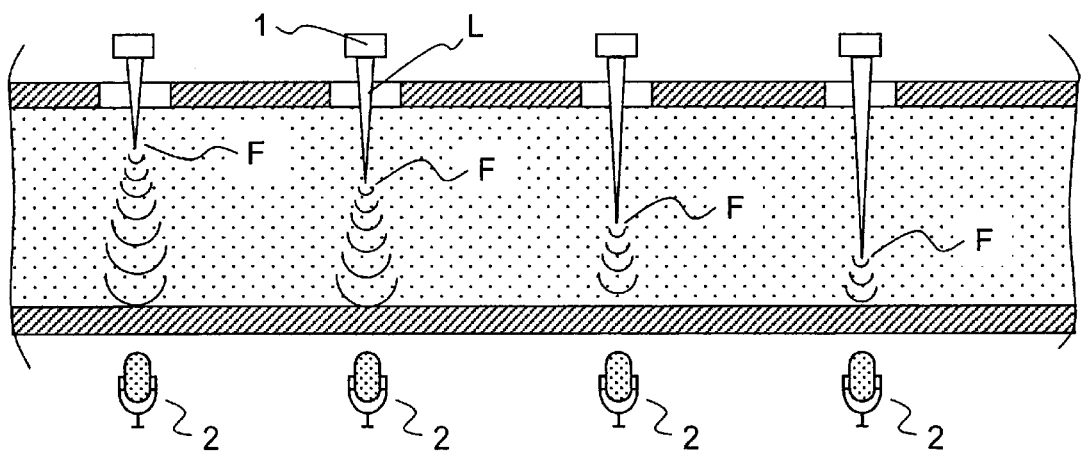
FIG. 5 is a schematic of a flow meter for determining a flow profile in accordance with a fifth embodiment.

FIG. 5 illustrates a further embodiment, by means of which it is possible to set up a density profile.

Present for this purpose are a plurality of focal points F in the medium M which have a different spacing from the walls of the tube R. The focal points F therefore form an array. As illustrated here, this array can be achieved by means of a plurality of light emitters 1 which are arranged along the tube R. However, it can also be achieved by means of a single light emitter 1 which has an electronically variable focusing optical system, and can therefore scan a cross-sectional plane through the medium M. The propagation time, and thus the density of the medium can be measured, in turn, by means of the at least one sound detector 2.

The power and/or wavelength of the light can be varied in all the abovedescribed embodiments. Further data on the medium, for example, on its composition or calorific value, can thereby be obtained in addition to the flow rate.

In addition, information on any instances of turbulence or laminar flows which may occur inside the tube R can be provided by analyzing a detected sound signal.

The flow meter according to the invention is suitable, in particular, as a gas meter for natural gas in industrial and domestic sectors.

List of Reference Symbols

R Tube
W Wall
M Medium
L Light pulses
F Focal point
S Sound wave
D Spacing between two sound detectors
D', D" Spacing from the focal point to the sound detector
1 First light emitter
1' Second light emitter
2 First sound detector
2' Second sound detector
3 Electronic evaluating system
4 Window

What is claimed is:

1. A method for measuring a flow rate of a flowing medium by means of detecting a sound wave transmitted by the medium, comprising the steps of: producing the sound wave in the medium by irradiating the medium with light, the light having a wavelength which is absorbed by the medium; measuring a propagation of time of the sound wave or a Doppler frequency of the sound wave in order to determine the flow velocity, measuring in addition a propagation time of the sound wave independently of the flow velocity in order to determine a density of the medium by means of a sound detector and a light emitter that are arranged in a plane at least approximately perpendicular to a flow direction in order to determine a density of the medium.

2. The method as claimed in claim 1, wherein a first sound wave is detected in the flow direction, and a second sound wave is detected counter to the flow direction in order to determine the flow velocity independent of an instant of a generation of the sound wave.

3. The method as claimed in claim 1, wherein a mass flow is determined from the flow velocity measurement and the density measurement.

4. The method as claimed in claim 1, wherein use is made of a plurality of focal points which are spatially separated from one another, and are at a different spacing from a tube flowed through by the medium in order to set up a density profile.

5. The method as claimed in claim 1, wherein the medium is natural gas and is irradiated by a laser with a wavelength of between 1.5 and 3.5 µm and with a pulse duration of at least approximately 200 ns.

6. A flow meter, comprising: a light emitter for producing a photoacoustic sound wave in a flowing medium, and having a sound detector arranged at a spacing from the light emitter, wherein the light emitter has a focusing optical system for focusing a light beam at a focal point inside the medium and a propagation time of the photoacoustic sound wave or a Doppler frequency change in the photoacoustic sound wave is measured in order to determine a flow velocity, the flow meter further including an arrangement of a second light emitter and a second sound detector in a plane at least approximately perpendicular to the flow direction of the medium for measuring a propagation time of a sound wave independently of the flow velocity in order to determine a density of the medium.

7. The flow meter as claimed in claim 6, wherein two light emitters and two sound detectors are present and the two light emitters have different powers or different wavelengths in order to produce two sound waves of different intensity such that the sound detectors can assign the signals to the individual light emitters.

8. The flow meter as claimed in claim 6, wherein the medium is natural gas and is irradiated by a laser with a wavelength between 1.5 and 3.5 $\mu$m, the laser is operated in a pulsed fashion, and the flow meter is used as a gas meter.

9. The flow meter as claimed in claim 6, wherein a mass flow is determined from the flow velocity measurement and the density measurement.

* * * * *